United States Patent [19]

Helwig et al.

[11] Patent Number: 4,703,072
[45] Date of Patent: Oct. 27, 1987

[54] TETRAHYDROFURANCARBOXYLIC ACID DERIVATIVES

[75] Inventors: Reinhard Helwig, Ludwigshafen; Peter Neumann, Wiesloch; Alexander Aumueller, Ludwigshafen; Hubert Trauth, Dudenhofen, all of Fed. Rep. of Germany

[73] Assignee: BASF Aktiengesellschaft, Ludwigshafen, Fed. Rep. of Germany

[21] Appl. No.: 874,864

[22] Filed: Jun. 16, 1986

[30] Foreign Application Priority Data

Jun. 25, 1985 [DE] Fed. Rep. of Germany ....... 3522678

[51] Int. Cl.$^4$ ............................................... C08K 5/34
[52] U.S. Cl. ..................................... 524/99; 524/103; 252/401; 252/403; 546/16; 546/187; 546/214
[58] Field of Search .................... 546/16, 187, 214; 524/99, 103; 252/401, 403

[56] References Cited

U.S. PATENT DOCUMENTS

| | | | |
|---|---|---|---|
| 2,077,422 | 4/1937 | Lazier | 549/503 |
| 2,082,025 | 6/1937 | Peters, Jr. | 549/503 |
| 3,265,711 | 8/1966 | Pioch | 546/214 |
| 3,449,368 | 6/1969 | Shen | 546/214 |
| 3,640,928 | 2/1972 | Murayama et al. | 546/188 |
| 3,684,765 | 8/1972 | Matsui et al. | 546/187 |
| 3,904,581 | 9/1975 | Murayama et al. | 524/103 |
| 4,049,647 | 9/1977 | Holt et al. | 546/187 |
| 4,141,883 | 2/1979 | Soma et al. | 546/187 |
| 4,603,205 | 7/1986 | Neumann et al. | 546/187 |
| 4,618,634 | 10/1986 | Cantatore et al. | 546/187 |

FOREIGN PATENT DOCUMENTS

| | | |
|---|---|---|
| 0103115 | 3/1984 | European Pat. Off. . |
| 2735051 | 2/1978 | Fed. Rep. of Germany . |
| 3117389 | 11/1982 | Fed. Rep. of Germany . |
| 3345376 | 6/1985 | Fed. Rep. of Germany ...... 546/214 |
| 139374 | 8/1984 | Japan .................................... 549/499 |

OTHER PUBLICATIONS

Chemical Abstracts, Band 88, nr. 2, 9 Jan. 1978, Columbus, Ohio.
Chemical Abstracts, Band 89, Nr. 14, 2 Oct. 1978, Columbus, Ohio.

*Primary Examiner*—John Kight
*Assistant Examiner*—Kriellion Morgan
*Attorney, Agent, or Firm*—Oblon, Fisher, Spivak, McClelland, & Maier

[57] ABSTRACT

Novel tetrahydrofurancarboxylic acid derivatives of the general formula I

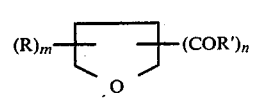

or polymers of these containing units of the formula II

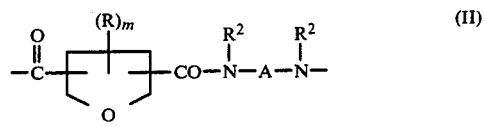

where the radicals R independently of one another are each $C_1$-$C_4$-alkyl, cyclohexyl or phenyl, m is from 0 to 3, n is 1 or 2, and R' is a radical of the formula

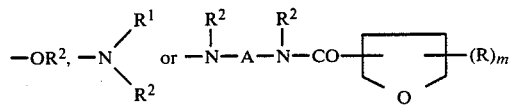

suitable terminal groups in the polymers being chlorine or hydroxyl in the case of the CO group and hydrogen in the case of the —$NR^2$ group, A is a bridge member, $R^1$ is hydrogen, $C_2$-$C_6$-alkenyl, $C_1$-$C_{12}$-alkyl which may be interrupted by up to 3 oxygen atoms, unsubstituted or substituted phenylalkyl or $C_5$-$C_7$-cycloalkyl and $R^2$ is radical of the formula

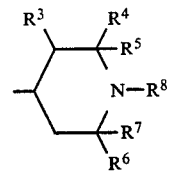

where $R^3$ is hydrogen or methyl, $R^4$, $R^5$, $R^6$ and $R^7$ are each methyl or ethyl and $R^8$ is hydrogen, $C_1$-$C_8$-alkyl, $C_3$-$C_8$-alkenyl, $C_2$-$C_4$-hydroxyalkyl or aralkyl, and salts of the compounds I and II, are very useful as light stabilizers for organic polymers.

6 Claims, No Drawings

TETRAHYDROFURANCARBOXYLIC ACID DERIVATIVES

It is known that 2,2,6,6-tetraalkylpiperidine derivatives are excellent light stabilizers for organic polymers. Other light stabilizers which have been described are various carboxylic acid derivatives of 5-membered oxygen heterocycles. These are furancarboxylic acid derivatives.

In a general form, esters of oxygen-containing heterocyclic carboxylic acids with 2,2,6,6-tetraalkylpiperidines are claimed in German Laid-Open Application DOS No. 2,258,752, and the corresponding esters with 2,2,36,6-pentaalkyl- and 1,2,2,3,6,6-hexaalkylpiperidines are claimed in German Laid-Open Application DOS No. 2,623,422. Oxygen-containing heterocyclic carboxamides of 1,2,2,6,6-pentaalkylpiperidines are embraced in general form by German Laid-Open Application DOS No. 2,349,962.

Finally, amides of tetrahydrofuran-2,5-dicarboxylic acid with 1,2,2,6,6-penta- and 1,2,2,3,6,6-hexaalkylpiperidines, which contain a phenolic group in the molecule, are described in EP-A-111 448, as a component of a recording material for color photography.

The present invention relates to tetrahydrofurancarboxylic acid derivatives of the general formula I

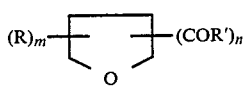

or polymers of these containing units of the formula II

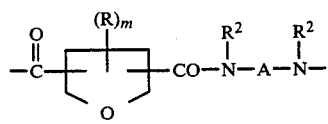

where the radicals R independently of one another are each $C_1$-$C_4$-alkyl, cyclohexyl or phenyl, m is from 0 to 3, n is 1 or 2, and R' is a radical of the formula

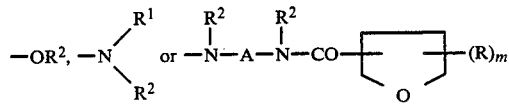

suitable terminal groups in the polymers being chlorine or hydroxyl in the case of the CO group and hydrogen in the case of the —$NR^2$ group, A is a bridge member, $R^1$ is hydrogen, $C_2$-$C_6$-alkenyl, $C_1$-$C_{12}$-alkyl which may be interrupted by up to 3 oxygen atoms, unsubstituted or substituted phenylalkyl or $C_5$-$C_7$-cycloalkyl and $R^2$ is a radical of the formula

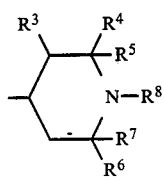

where $R^3$ is hydrogen or methyl, $R^4$,$R^5$,$R^6$ and $R^7$ are each methyl or ethyl and $R^8$ is hydrogen, $C_1$-$C_8$-alkyl, $C_3$-$C_8$-alkenyl, $C_2$-$C_4$-hydroxyalkyl or aralkyl, and salts of the compounds I and II.

According to the general definition, alkyl radicals R are the straight-chain or branched groups $C_nH_{2n+1}$, the straight-chain radicals being preferred. Specific examples are:

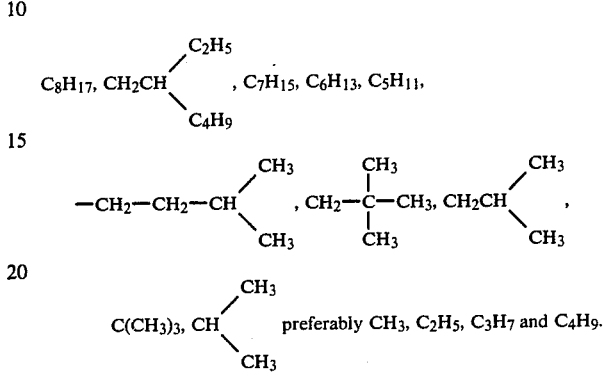

Examples of alkyl groups $R^1$ containing etheroxygen atoms are: $(CH_2)_3OCH_3$, $(CH_2)_3OC_2H_5$ $H$, $(CH_2)_3OC_3H_7$, $(CH_2)_3OC_4H_9$, $(CH_2)O(CH_2)_2OCH_3$, $(CH_2)_2O(CH_2)_2OC_2H_5$, $(CH_2)_2O(CH_2)_2OC_3H_7$, $(CH_2)_3O(CH_2)_2OC_4H_9$, $(C_2H_4O)_3CH_3$, $(C_2H_4O)_3C_2H_5$, $(C_2H_4O)_3C_4H_9$,

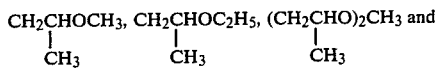

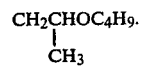

Alkenyl is, for example, vinyl, allyl, methallyl or 2-butenyl.

Examples of phenylalkyl radicals $R^1$ are $(CH_2)_qC_6H_5$, $(CH_2)_qC_6H_4OCH_3$, $(CH_2)qC_6H_3(OCH_3)_2$, $(CH_2)qC_6H_4CH_3$ and $(CH_2)qC_6H_4Cl$, where q is from 1 to 4.

Examples of cycloalkyl radicals $R^1$ are cyclopentyl, cyclohexyl and cycloheptyl.

Examples of alkenyl, hydroxyalkyl and aralkyl radicals $R^8$ are:

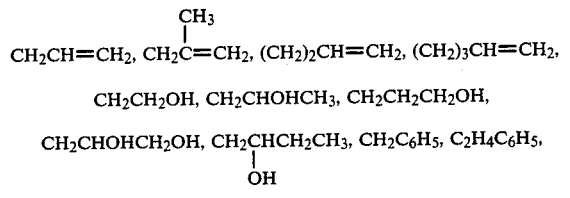

$CH_2C_6H_4CH_3$ and $CH_2C_6H_4Cl$.

Bridge members A are, in particular, $C_2$-$C_{12}$-alkylene and radicals of the formulae

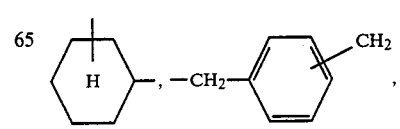

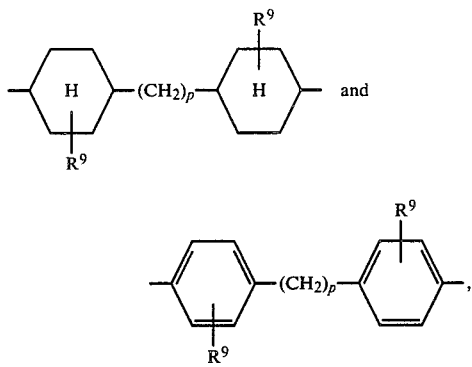

where $R^9$ is hydrogen or methyl and p is 0, 1 or 2.

Specific examples of alkylene are $C_2H_4$, $(CH_2)_3$, $(CH_2)_4$, $(CH_2)_6$, $(CH_2)_2O(CH_2)_2$, $(CH_2)_3O(CH_2)_3$, $(CH_2)_3O(CH_2)_2O(CH_2)_3$.

In preferred compounds of the formula I, R is hydrogen or methyl, $R^3$ is hydrogen and $R^4$, $R^5$, $R^6$ and $R^7$ are each methyl.

The novel compounds can be prepared by well known chemical methods. For example, an important method for obtaining the compounds according to the invention is the catalytic hydrogenation of appropriate furan derivatives. Furan derivatives of this type are known. For example, German Patent Nos. 1,929,928 and 2,258,752 mention piperidyl esters, and German Patent Nos. 2,040,975 and 2,349,962 mention piperidylamines of furan-2-carboxylic acid. Patent Application No. P 33 45 376.4 embraces piperidyl esters and piperidylamides of various furan-3-carboxylic acids. Other compounds which to date have not been described in detail, for example derivatives of furan-2,5-dicarboxylic acid, of furan-3,4-dicarboxylic acid, of 2,5-dimethylfuran-3,4-dicarboxylic acid, etc., can also be prepared in a similar manner. All compounds of this type can be subjected to catalytic hydrogenation under suitable conditions, without difficulty; depending on the substitution of the furan ring, various stereoisomers may be formed, but this does not have an adverse effect on the stabilizing activity.

Another route to the novel compounds starts from methyl or ethyl tetrahydrofurancarboxylate or the corresponding acyl chlorides, where these are known. The alkyl tetrahydrofurancarboxylates can be subjected to transesterification with, for example, the desired 4-hydroxypiperidines in the presence of catalytic compounds such as alkali metal alcoholates or titanium tetrabutylate, the corresponding lower alcohol being removed by distillation. The tetrahydrofurancarbonyl chlorides can be reacted with 4-aminopiperidine derivatives in the presence of an acid acceptor, such as an alkali metal carbonate or an organic amine, to give the corresponding amides.

The preparation of a large number of furan- or tetrahydrofurancarboxylic acid or -dicarboxylic acid derivatives, which are required as starting compounds, is described in the literature. In many cases, preparation methods known from the literature can also be used without difficulty for furan- or tetrahydrofurancarboxylic acid derivatives which have not been described to date.

The novel compounds may be in the form of the free bases or of salts. Suitable anions are derived from, for example, inorganic acids and in particular organic carboxylic acids.

Examples of inorganic anions are chloride bromide, sulfate, methosulfate, phosphate or thiocyanate.

Examples of carboxylic acid anions are formate, acetate, propionate, hexanoate, cyclohexanoate, lactate, stearate, dodecylbenzoate, benzoate, acrylate, methacrylate, citrate, malonate and succinate, as well as anions of polycarboxylic acids possessing up to 100 COOH groups.

The examples which follow illustrate the preparation.

Compounds according to the invention are useful for stabilizing organic material, especially plastics, to degradation by light and heat. They are added to the plastics to be stabilized in a concentration of from 0.01 to 5, preferably from 0.02 to 1, % by weight, before, during or after polymer formation.

Mixing of the novel compounds with the plastics to be stabilized can be carried out using any conventional apparatus or method for mixing stabilizers or other additives into polymers.

The plastics stabilized by one of the compounds according to the invention may furthermore contain other additives, for example antioxidants, light stabilizers, metal deactivators, antistatic agents, flame retardants, pigments and fillers.

Antioxidants and light stabilizers which may be added to the plastics in addition to the novel compounds are, for example, compounds based on sterically hindered phenols or sulfur-containing or phosphorus-containing costabilizers.

Examples of phenolic antioxidants of this type are 2,6-di-tert-butyl-4-methylphenol, n-octadecyl-$\beta$-(3,5-di-tert-butyl-4-hydroxyphenyl)-propionate, 1,1,3-tris-(2-methyl-4-hydroxy-5-tert-butylphenyl)-butane, 1,3,5-trimethyl-2,4,6-tris-(3,5-di-tert-butyl-4-hydroxybenzyl)-benzene, 1,3,5-tris-(3,5-di-tert-butyl-4-hydroxybenzyl) isocyanurate, 1,3,5-tris-[$\beta$(3,5-di-tert-butyl-4-hydroxyphenyl)-propio-nyloxyethyl]isocyanurate, 1,3,5-tris-(2,6- dimethyl-3-hydroxy-4-tert-butylbenzyl) isocyanurate, pentaerythritol tetrakis-[$\beta$-(3,5-di-tert-butyl-4-hydroxyphenyl)propionate]etc.

Examples of phosphorus-containing antioxidants are tris-(nonylphenyl) phosphite, distearyl pentaerythritol diphosphite, tris-(2,4-di-tert-butylphenyl) phosphite, tris-(2-tert-butyl-4-methylphenyl) phosphite, bis-(2,4-di-tert-butylphenyl) pentaerythritol diphosphite, tetrakis(2,4-di-tert-butylphenyl) 4,4'-biphenylenediphosphite, etc.

Examples of sulfur-containing antioxidants are dilauryl thiodipropionate, dimyristyl thiodipropionate, distearyl thiodipropionate, pentaerythritol tetrakis($\beta$-laurylthiopropionate), pentaerythritol tetrakis-($\beta$-hexylthiopropionate), etc.

Other antioxidants and light stabilizers which may be used together with the novel compounds are, for example, 2-(2'-hydroxyphenyl)-benzotriazoles, 2-hydroxybenzophenones, aryl esters of hydroxybenzoic acids, $\alpha$-cyanocinnamic acid derivatives, nickel compounds and oxalic acid dianilides.

Examples of organic polymers which can be stabilized with the compounds according to the invention are: polymers of mono- and diolefins, e.g. low density or high density polyethylene, linear low density polyethylene, polypropylene, polyisobutylene, polybut-1-ene, polymethylpent-1-ene, polyisoprene and polybutadiene, and copolymers of mono- and diolefins, as well as blends of the stated polymers; copolymers of mono- or diolefins with other vinyl monomers, e.g. ethylene/alkyl acrylate copolymers, ethylene/alkyl methacrylate copolymers, ethylene/vinyl acetate copolymers or ethylene/acrylic acid copolymers; polystyrene; copolymers of styrene or α-methylstyrene with dienes or acryl derivatives, e.g. styrene/butadiene, styrene/acrylonitrile, styrene/ethyl methacrylate, styrene/butadiene/ethyl acrylate or styrene/acrylonitrile/methacrylate; ABS, MBS or similar polymers; halogen-containing polymers, e.g. polyvinyl chloride, polyvinyl fluoride, polyvinylidene fluoride and their copolymers; polymers which are derived from αβ-unsaturated acids and their derivatives, such as polyacrylates and polymethacrylates, polyacrylamides and polyacrylonitriles; polymers which are derived from unsaturated alcohols and amines or their acrylyl derivatives or acetals, such as polyvinyl alcohol or polyvinyl acetate; and polyurethanes, nylons, polyureas, polyesters, polycarbonates, polysulfones and polyethersulfones.

Other organic polymers which can be stabilized with the compounds according to the invention are industrial coatings. Particularly noteworthy among these are baking finishes, especially automotive finishes, preferably two-coat finishes.

Here too, the antioxidants and light stabilizers stated above may also be used.

Solid compounds according to the invention can be added to the coating in solid or dissolved form, while liquid compounds according to the invention may be added as such. Their good solubility in coating systems is particularly advantageous.

The novel compounds are preferably used in polyolefins, preferably ethylene polymers and propylene polymers, as well as in coating systems.

In view of the prior art, it was surprising, and could not be foreseen, that the desired compounds of the formulae I and II would have an excellent stabilizing effect on polymers and furthermore would possess outstanding compatibility with polymers, especially polyolefins.

EXAMPLE 1

2,2,6,6-Tetramethyl-4-piperidyl
2,5-dimethyltetrahydrofuran-3-carboxylate

Method A 15 g of 2,2,6,6-tetramethyl-4-piperidyl 2,5-dimethylfuran-3-carboxylate, 150 ml of methanol and 3 g of Raney nickel are introduced into a 0.3 l hydrogenation autoclave and hydrogenation is carried out at 150° C. and under 160 bar until the pressure remains constant, which takes about 5 hours. Thereafter, the mixture is filtered off from the Raney nickel and is evaporated down. GC-MS analysis indicates the presence of two isomeric principal products in a ratio of about 12:88, according to gas chromatography. Distillation under reduced pressure gives 12 g of the product of boiling point 120°-126° C./0.5 mbar in the form of a colorless oil.

Method B 80 g of methyl 2,5-dimethylfuran-3-carboxylate, 80 ml of methanol and 5 g of Raney nickel are introduced into a 0.3l hydrogenation autoclave, and hydrogenation is carried out at 150° C. and under 160 bar until the pressure remains constant. Thereafter, the mixture is filtered off from the Raney nickel and is evaporated down, and the residue is distilled under reduced pressure. 41 g of product of boiling point 28°-30° C./0.1 mbar are obtained as a colorless liquid.

31.6 g of methyl 2,5-dimethyltetrahydrofuran-3-carboxylate are heated with 31.4 g of 2,2,6,6-tetramethyl-4-piperidyl and 2 g of tetrabutyl ortho-titanate at 200° C. for 7 hours under a descending condenser. After cooling, the residue is dissolved in ethyl acetate, and the solution is washed with 5% strength sodium carbonate solution and water, dried and evaporated down. Distillation under reduced pressure gives the product in the form of a colorless oil of boiling point 120°-126° C./0.5 mbar.

EXAMPLE 2

2,2,6,6-Tetramethyl-4-piperidyl tetrahydrofuran-2-carboxylate 15 g of 2,2,6,6-tetramethyl-4-piperidyl furan-2-carboxylate, 150 ml of methanol and 3 g of Raney nickel are introduced into a 0.3 l hydrogenation autoclave, and hydrogenation is carried out at 100° C. and under 100 bar until the pressure remains constant, which takes about 6 hours. The Raney nickel is filtered off, the filtrate is evaporated down and the residue is distilled under reduced pressure to give 11.5 g of a colorless oil of boiling point 118°-122° C./1.3 mbar.

EXAMPLE 3

2,2,6,6-Tetramethyl-4-piperidyl
2,4-dimethyltetrahydrofuran-3-carboxylate

By hydrogenating 2,2,6,6-tetramethyl-4-piperidyl 2,4-dimethylfuran-3-carboxylate by a method similar to that described in Example 1 A, a colorless oil of boiling point 114° C./0.1 mbar (2 isomers in a ratio of 10:90) is obtained.

EXAMPLE 4

2,5-Dimethyltetrahydrofuran-3-carboxylic acid
N-butyl-N-(2,2,6,6-tetramethyl-4-piperidyl)-amide By hydrogenating 2,5-dimethylfuran-3-carboxylic acid N-butyl-N-(2,2,6,6-tetramethyl-4-piperidyl)-amide by a method similar to that described in Example 1 A, the product (2 isomers in a ratio of 5:95 according to gas chromatography) is obtained in the form of a colorless viscous mass.

EXAMPLE 5

Salt of 2,5-dimethyltetrahydrofuran-3-carboxylic acid
N-butyl-N-(2,2,6,6-tetramethyl-4-piperidyl)-amide and
adipic acid 10.14 g of the carboxamide from Example 4 and 2.2 g of adipic acid in methanol are stirred until a clear solution has formed. This solution is evaporated to dryness under reduced pressure from a water pump, and the residue is powdered. It has a melting point of 77°-79° C.

EXAMPLE 6

Bis-(N-1,6-hexamethylene-N-1,2,2,6,6-pentamethyl-4-piperidly)-2,5-dimethyltetrahydrofuran-3-carboxamide By hydrogenating bis-(N-1,6-hexamethylene-N-1,2,2,6,6-pentamethyl-4-piperidyl)-2,5-dimethylfuran-3-carboxamide by a method similar to that described in Example 1 A, the product is obtained as a virtually colorless viscous mass.

EXAMPLE 7

Bis-(N-1,2-ethylene-N-1,2,2,6,6-pentamethyl-4-piperidyl)-2,5-dimethyltetrahydrofuran-3-carboxamide By hydrogenating bis-(N-1,2-ethylene-N-1,2,2,6,6-pentamethyl-4-piperidyl)-2,5-dimethylfuran-3-carboxamide (m.p. 222°–224° C.) by a method similar to that described in Example 1 A, the product is obtained as a viscous mass.

EXAMPLE 8

Bis-(N-1,2-ethylene-N-2,2,6,6-tetramethyl-4-piperidyl)-2,4-dimethyltetrahydrofuran-3-carboxamide By hydrogenating bis-(N-1,2-ethylene-N-2,2,6,6-tetramethyl-4-piperidyl)-2,4-dimethylfuran-3-carboxamide (m.p. 237°–238° C.) by a method similar to that described in Example 1 A, the product is obtained as a viscous mass.

EXAMPLE 9

Bis-(N-1,6-hexamethylene-N-2,2,6,6-tetramethyl-4-piperidyl)tetrahydrofuran-2-carboxamide The starting compound, bis-(N-1,6-hexamethylene-N-2,2,6,6-tetramethyl-4-piperidyl)-furan-2-carboxamide, is prepared by refluxing 2 parts of fur-2-oyl chloride, 1 part of bis-4-(1,6-hexamethyleneamino)-2,2,6,6-tetramethylpiperidine and 1 part of anhydrous sodium carbonate in toluene for 24 hours. After cooling, the precipitate is dried and suspended in water, and the suspension is brought to an alkaline pH by the dropwise addition of sodium hydroxide solution. The mixture is filtered under suction and the residue is washed neutral and dried to give the product of melting point 110°–112° C. Hydrogenation is carried out by a method similar to that described in Example 2 and takes about 9 hours. The product is obtained in the form of a slightly brownish resinous mass.

Other compounds according to the invention are listed in Table 1.

TABLE 1

Compounds of the formula

R³—[ring with O]—R¹, R² on carbons

| Example | R¹ | R² | R³ | R⁴ |
|---------|----|----|----|----|
| 10 | 2,2,6,6-tetramethyl-1-methyl-4-piperidinyl ester (–COO–piperidine with N–CH₃) | H | H | H |
| 11 | 2,2,6,6-tetramethyl-4-piperidinyl N-butyl carboxamide (–CON(C₄H₉)–piperidine, NH) | H | H | H |
| 12 | 2,2,6,6-tetramethyl-4-piperidinyl N-(3-methoxypropyl) carboxamide (–CON((CH₂)₃OCH₃)–piperidine, NH) | H | H | H |
| 13 | bis(2,2,6,6-tetramethyl-4-piperidinyl) hexamethylene bis-carboxamide: tetrahydrofuranyl–CO–N–(CH₂)₆–N–CO– linking two 2,2,6,6-tetramethyl-4-piperidinyl(NH) groups | H | H | H |

TABLE 1-continued
Compounds of the formula $$\begin{array}{c} R^2 \quad R^1 \\ \diagup O \diagdown \\ R^3 \quad R^4 \end{array}$$

| | $R^1$ | $R^2$ | $R^3$ | $R^4$ |
|---|---|---|---|---|
| 14 | ![structure: two 2,2,6,6-tetramethylpiperidine units with N–CH₃, each linked via CO–N to (CH₂)₆ bridge, with tetrahydrofuran-2-yl–CO group] | H | H | H |
| 15 | ![structure: two N–H piperidine units linked to cyclohexyl-CH₂-cyclohexyl bridge via N–CO, with tetrahydrofuran-2-yl–CO group] | H | H | H |
| 16 | ![structure: 2,2,6,6-tetramethyl-4-(COO–)piperidine, NH] | H | H | CH₃ |
| 17 | ![structure: 2,2,6,6-tetramethyl-4-(COO–)piperidine, NH] | H | H | ![structure: 2,2,6,6-tetramethyl-4-(COO–)piperidine, NH] |
| 18 | ![structure: 2,2,6,6-tetramethyl-4-(COO–)piperidine, N–CH₃] | H | H | ![structure: 2,2,6,6-tetramethyl-4-(COO–)piperidine, N–CH₃] |

TABLE 1-continued
Compounds of the formula
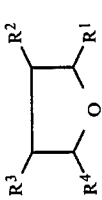
| | $R^1$ | $R^2$ | $R^3$ | $R^4$ |
|---|---|---|---|---|
| 19 | 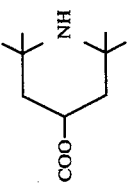 | H | H | 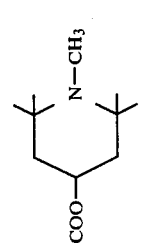 |
| 20 | H | 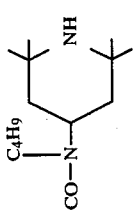 | H | H |
| 21 | H | 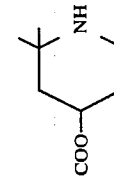 | H | H |
| 22 | H |  | H | H |
| 23 | $CH_3$ |  | H | H |

TABLE 1-continued
Compounds of the formula
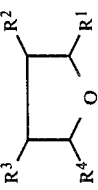
| | $R^1$ | $R^2$ | $R^3$ | $R^4$ |
|---|---|---|---|---|
| 24 | $CH_3$ | 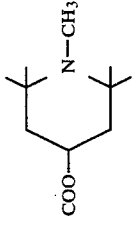 | H | H |
| 25 | $CH_3$ | 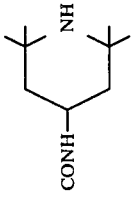 | $CH_3$ | H |
| 26 | $CH_3$ | 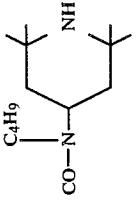 | $CH_3$ | H |
| 27 | $CH_3$ | 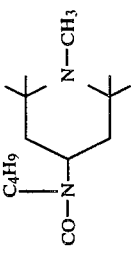 | $CH_3$ | H |
| 28 | $CH_3$ |  | $CH_3$ | H |

TABLE 1-continued

Compounds of the formula $$\begin{array}{c} R^2 \quad R^1 \\ R^3 \quad R^4 \end{array} O$$

| | $R^1$ | $R^2$ | $R^3$ | $R^4$ |
|---|---|---|---|---|
| 29 | $CH_3$ | (structure) | $CH_3$ | H |
| 30 | $CH_3$ | (structure) | $CH_3$ | H |
| 31 | $CH_3$ | (structure) | $CH_3$ | H |

TABLE 1-continued

Compounds of the formula $$\begin{array}{c} R^2 \quad R^1 \\ \diagup \quad \diagdown \\ \quad O \\ \diagup \quad \diagdown \\ R^3 \quad R^4 \end{array}$$

| | $R^1$ | $R^2$ | $R^3$ | $R^4$ |
|---|---|---|---|---|
| 32 | $CH_3$ | 2,2,6,6-tetramethyl-1-methyl-piperidin-4-yl-OOC— | H | $CH_3$ |
| 33 | $CH_3$ | 2,2,6,6-tetramethyl-1-(2-hydroxyethyl)-piperidin-4-yl-OOC— | H | $CH_3$ |
| 34 | $CH_3$ | 2,2,6,6-tetramethyl-piperidin-4-yl-HNOC— | H | $CH_3$ |
| 35 | $CH_3$ | 2,2,6,6-tetramethyl-1-methyl-piperidin-4-yl-HNOC— | H | $CH_3$ |
| 36 | $CH_3$ | 2,2,6,6-tetramethyl-1-methyl-piperidin-4-yl-($C_4H_9$)NOC— | H | $CH_3$ |

TABLE 1-continued
Compounds of the formula
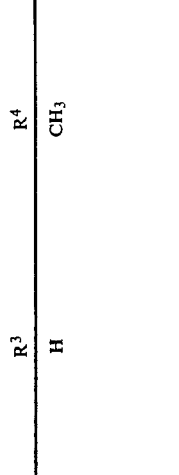
| | $R^1$ | $R^2$ | $R^3$ | $R^4$ |
|---|---|---|---|---|
| 37 | $CH_3$ |  | H | $CH_3$ |
| 38 | $CH_3$ |  | H | $CH_3$ |
| 39 | $CH_3$ | 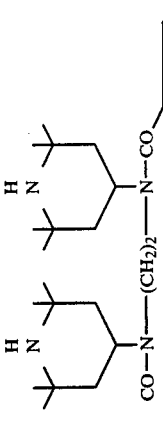 | H | $CH_3$ |
| 40 | $CH_3$ |  | H | $CH_3$ |

TABLE 1-continued

Compounds of the formula $$\begin{array}{c} R^2 \quad R^1 \\ R^3 \diagdown\!\!\!\!\diagup O \\ R^4 \end{array}$$

| | $R^1$ | $R^2$ | $R^3$ | $R^4$ |
|---|---|---|---|---|
| 41 | CH₃ | ![structure with H₃C-CH-CH₂ linker between two tetramethylpiperidine-CO-N groups and tetrahydrofuran] | H | CH₃ |
| 42 | CH₃ | ![structure with -(CH₂)₄- linker between two tetramethylpiperidine-CO-N groups and tetrahydrofuran] | H | CH₃ |
| 43 | CH₃ | ![structure with -(CH₂)₆- linker between two tetramethylpiperidine-CO-N groups and tetrahydrofuran] | H | CH₃ |

TABLE 1-continued
Compounds of the formula
$$\begin{array}{c} R^2 \\ R^3 \\ R^4 \end{array} \begin{array}{c} R^1 \\ O \end{array}$$
| | $R^1$ | $R^2$ | $R^3$ | $R^4$ |
|---|---|---|---|---|
| 44 | CH₃ | ![structure with two cyclohexyl-CH₂ linked piperidine amide groups] | H | CH₃ |
| 45 | CH₃ | ![piperidine-COO- with NH] | CH₃ | CH₃ |
| 46 | CH₃ | ![piperidine-COO- with NH] | H | t-C₄H₉ |
| 47 | CH₃ | ![piperidine-COO- with NH] | C₂H₅ | H |
| 48 | CH₃ | ![piperidine-COO- with NH] | H | 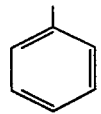 |

TABLE 1-continued

Compounds of the formula

| Bsp | R¹ | R² | R³ | R⁴ |
|---|---|---|---|---|
| 49 | H |  |  | H |
| 50 | H |  |  | H |
| 51 | CH₃ |  |  | CH₃ |
| 52 | Salt of compound of Example 11 and adipic acid | | | |
| 53 | Salt of compound of Example 11 and polyacrylic acid (about 28–42 units) | | | |
| 54 | Salt of compound of Example 27 and 2,4-dimethylglutaric acid | | | |
| 55 | Salt of compound of Example 27 and adipic acid | | | |
| 56 | Salt of compound of Example 30 and 2-ethylhexanoic acid | | | |
| 57 | Salt of compound of Example 4 and polyacrylic acid (about 28–42 units) | | | |
| 58 | Salt of compound of Example 4 and polyacrylic acid (about 70 units) | | | |
| 59 | Salt of compound of Example 43 and adipic acid | | | |
| 60 | Salt of compound of Example 43 and 2-ethylhexanoic acid | | | |

EXAMPLE 61

N-2-(2,4-Dimethoxyphenyl)-ethyl-N-2,2,6,6-tetramethyl-4-piperidyl-2,5-dimethyltetrahydrofuran-3-carboxamide By hydrogenating 10.0 g of N-2-(2,4-dimethoxyphenyl)-ethyl-N-2,2,6,6-tetramethyl-4-piperidyl-2,5-dimethylfuran-3-carboxamide as described in Example 1 A, 5.90 mg of a slightly yellowish oil which cannot be distilled are obtained.

EXAMPLE 62

Salt of bis-(N-1,6-hexylene-N-2,2,6,6-tetramethyl-4-piperidyl-tetrahydrofuran-3-carboxamide and adipic acid 9.0 g of a colorless solid of melting point 250°–252° C. are obtained from 9.1 g of bis-(N-1,6-hexylene-N-2,2,6,6-tetramethyl-4-piperidyltetrahydrofuran-3-carboxamide and 1.14 g of adipic acid as described in Example 5.

EXAMPLE 63

Salt of 2,2,6,6-tetramethyl-4-piperidyl 2,5-dimethyltetrahydrofuran-3-carboxylate and adipic acid 14.0 g of a colorless solid of melting point 182°–184° C. are obtained from 11.2 g of 2,2,6,6-tetramethyl-4piperidyl 2,5-dimetIyltetrahydrofuran-3-carboxylate and 2.95 g of adipic acid as described in Example 5.

EXAMPLE OF USE 0.25 part of the compound from Example 1 is incorporated into 100 parts of polypropylene (1320 H from BASF) by extruding the material twice at 220° C., and the extruded material is compressed to give 200 μm thick sheets. After the sheets have been stored for 14 days in the dark at 25° C., their surface does not show any coating.

The sheets produced in this manner are subjected to weathering in the open air. Aging is determined by measuring the CO number after particular intervals of time. The onset of embrittlement is determined mechanically and is found to correspond to a CO number of about 50. After one year, the two sheets tested have CO humbers of 3.33 and 5.73. The surfaces of the sheets are clear.

Two sheets which are produced in the same manner but contain 0.25 part of Chimassorb 944 instead of the compound from Example 1 have CO numbers of 7.22 and 11.0 after one year. Their surfaces exhibit a haze.

We claim:

1. A tetrahydrofurancarboxylic acid derivative of the formula I

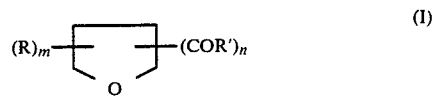

where the radicals R independently of one another are each $C_1$–$C_4$-alkyl, cyclohexyl or phenyl, m is from 0 to 3, n is 1 or 2, and R′ is a radical of the formula

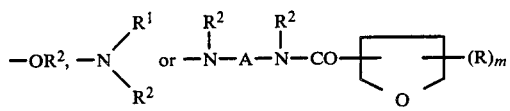

A is a bridge member, $R^1$ is hydrogen, $C_2$–$C_6$-alkenyl, $C_1$–$C_{12}$-alkyl which may be interrupted by up to 3 oxygen atoms, unsubstituted or substituted phenylalkyl or $C_5$–$C_7$-cycloalkyl and $R^2$ is a radical of the formula

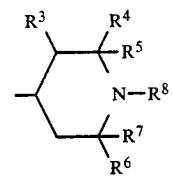

where $R^3$ is hydrogen or methyl, $R^4$, $R^5$, $R^6$ and $R^7$ are each methyl or ethyl and $R^8$ is hydrogen, $C_1$–$C_8$-alkyl, $C_3$–$C_8$-alkenyl, $C_2$–$C_4$-hydroxyalkyl or aralkyl, and salts of the compound I and.

2. A compound as claimed in claim 1, wherein A is $C_2$–$C_{12}$-alkylene or aralkylene radical.

3. A compound as claimed in claim 1, wherein $R^3$ is hydrogen and $R^4$, $R^5$, $R^6$ and $R^7$ are each methyl.

4. A compound as claimed in claim 1, wherein $R^8$ is hydrogen or methyl.

5. A compound as claimed in claim 1, wherein R is methyl.

6. A stabilized organic material containing a compound as claimed in claim 1.

* * * * *